US007118924B2

(12) United States Patent
Coccia et al.

(10) Patent No.: US 7,118,924 B2
(45) Date of Patent: Oct. 10, 2006

(54) METHOD FOR PRODUCING HUMAN ANTIBODIES IN SCID MICE WHICH USES DENDRITIC CELLS PULSED WITH ANTIGEN-ANTIBODY COMPLEXES AND ANTIGEN-ANTIBODY COMPLEXES AS IMMUNIZING AGENTS

(75) Inventors: Marco Anthony Coccia, San Diego, CA (US); Peter Brams, San Diego, CA (US)

(73) Assignee: Biogen IDEC Inc., Cambridge, MA (US)

( * ) Notice: Subject to any disclaimer, the term of this patent is extended or adjusted under 35 U.S.C. 154(b) by 426 days.

(21) Appl. No.: 09/798,525

(22) Filed: Feb. 21, 2001

(65) Prior Publication Data

US 2002/0044930 A1  Apr. 18, 2002

Related U.S. Application Data

(63) Continuation of application No. 09/149,479, filed on Sep. 8, 1998, now abandoned.

(60) Provisional application No. 60/057,831, filed on Sep. 8, 1997.

(51) Int. Cl.
*G01N 33/53* (2006.01)
*G01N 33/00* (2006.01)
*G01N 33/563* (2006.01)
*G01N 33/536* (2006.01)
*A01N 63/00* (2006.01)

(52) U.S. Cl. .................. 436/547; 436/86; 436/512; 436/536; 424/93.7; 424/93.71; 424/184.1; 424/193.1; 424/277.1; 424/388.15; 424/388.22; 530/388.8; 530/388.85; 530/380; 530/385; 530/386; 530/387.1; 530/388.15; 530/388.22

(58) Field of Classification Search ............. 424/184.1, 424/193.1, 277.1, 93.71, 93.7; 530/388.15, 530/388.22, 388.8, 388.85, 380, 385, 386, 530/387.1; 436/512, 86, 536, 547; 435/440
See application file for complete search history.

(56) References Cited

U.S. PATENT DOCUMENTS 5,663,481 A     9/1997  Gallinger et al.
5,672,480 A     9/1997  Dowell et al.
5,681,729 A  * 10/1997  Kudo et al.
6,432,653 B1 *  8/2002  Okarma
6,497,876 B1 * 12/2002  Maraskovsky

OTHER PUBLICATIONS

Stein, S.H. et al, Eur. J. Immunol. 20: 403-407, 1990.*
Kunkl, A. et al., Immunology 43: 371- 1981.*
Tjoa, B. et al, The Prostate, 28: 65-69, 1996.*
Yoshida, K. et al, Immunology, 84: 117-126, 1995.*
Yoshida, K. et al. Eur. J. Immunol. 24: 464-468, 1994.*

Cella et al., "Ligation of CD40 on Dendritic Cells Triggers Production of High Levels of Interleukin-12 and Enhances T Cell Stimulatory . . . ", J. Exp. Med., vol. 184 Aug. 1996 pp. 747-752.
Couglan et al., "Enhanced Proliferation of CD4+ T Cells Induced by Dendritic Cells Following Antigen Uptake in the Presence of . . . ", Vet. Immunology and Immunopathology, vol. 49 (1996) pp. 321-330.
Garner et al., "Low Expression of CD20 and CD23 in Epstein-Barr Virus-Induced B-Cell Tumors in SCID/hu Mice", American Jour. of Pathology, vol. 142, No. 2 (Feb. 1993) pp. 353-358.
Grossman et al., "Antitumor Responses Induced by Transgenic Expression of CD40 Ligand", Human Gene Therapy 8:1935-1943 (Nov. 1997).
Heufler et al., "Interleukin-12 is Produced by Dendritic Cells and Mediates T-Helper 1 Development as well as Interferon-y Production by T Helper 1 Cells" Eur. J. Immuno. (1996) 26:659-668.
Kato et al., "Gene Transfer of CD40-Ligand Induces Autologous Immune Recognition of Chronic Lymphocytic Leukemia B Cells", J. Clin. Invest., vol. 101, No. 5 (Mar. 1998) pp. 1133-1141.
Nishioka et al., "The Role of CD40-CD40 Ligand Interaction in Human T Cell-B Cell Collaboration" Amer. Assoc. of Immunologists, (1994) pp. 1027-1036.
Tjoa et al., "Presentation of Prostate Tumor Antigens by Dendritic Cells Stimulates T-Cell Proliferation and Cytotoxicity", The Prostate 28:65-69 (1996).
Koch et al., Brief Definitive Report "High Level IL-12Production of Murine Dendritic Cells: Upregulation via MHC Class II and . . . ", Depts.of Dermatology, Univs. of Innsbruck, Wurzburg and Erlagene-Nurnberg Rec'd for publicaton Mar. 1996; revised Jun. 1996; pp. 741-746.
Marco A. Coccia et al., "High Titer, Prostate Specific Antigen-Specific Human IgG Production by hu-PBL-SCID Mice Immunized with Antigen-Mouse IgG2a Complex-Pulsed Autologous Dendritic Cells," The Journal of Immunology, The American Assocation of Immunologists, p. 5772-5780, 1998.
Tary-Lehmann et al., J. Exp. Med., 1992, 175(2):503-516 (full text).
Somasundarum et al., Clin. Exp. Immunol., 1995, 101:94-99 (full text).
Martino et al., Eur. J. Immunol., 1993, 23(5):1023-1028 (full text).
Cella et al. (1997) Origin, maturation and antigen presenting function of dendritic cells. *Curr. Opin. Immunol.*, 9(1):10-16.
Peters et al. (1996) Dendritic cells: from ontogenic orphans to myelomonocytic descendants. *Immunology Today* 17(6):273-282.
Romani et al. (1994) Proliferating dendritic cell precursors in human blood. *J. Exp. Med.* 180:83-93.
Caux et al. (1995) Human dendritic Langerhans cells generated in vitro frim CD34+ progenitors can prime naive CD4+ T cells and process soluble antigen. *J. Immunol.* 155:5427-5435.

(Continued)

*Primary Examiner*—Alana M. Harris
(74) *Attorney, Agent, or Firm*—Pillsbury Winthrop Shaw Pittman LLP (57) ABSTRACT

An improved method for producing human antibodies in SCID mice is provided. The improvement includes the use of dendritic cells pulsed with antigen-antibody complexes and antigen-antibody complexes as immunizing agents.

17 Claims, 8 Drawing Sheets

OTHER PUBLICATIONS

Santiago-Schwartz et al. (1995) Stem cell factor enhances dendritic cell development, *Dendritic Cells in Fundamental and Clinical Immunology*, vol. 2, Ed. by J. Bancherau et al., Plenum Press, NY, 1995.

Linsley et al. (1991) Binding of the B cell activation antigen B7.1 to CD28 costimulates T cell proliferation and interleukin 2 mRNA accumulation. *J. Exp. Med.* 173(3):721-730.

Caux et al. (1994) B70/B7.2 is identical to CD86 and is the major functional ligand for CD28 expressed on human dendritic cells. *J. Exp. Med.* 180(5): 1841-1847.

Bakker et al. (1995) Generation of cytotoxic T lymphocytes from healthly donors after presentation of melanoma-associated antigen derived epitopes by dendritic cells in vitro. *Cancer Res.* 55:5330-5334.

Van Elsas et al. (1996) Peptide pulsed dendritic cells induce tumorcidal cytotoxic T lymphocytes from healthy donors against stably HLA-A*0201-binding peptides from the Melan-A/MART-1 self antigen. *Eur. J. Immunol.* 26: 1683-1689.

Fanger et al. (1996) Type 1 (CD64) and type II (CD32) FcγR receptor-mediated phagocytosis by human blood dendritic cells. *J. Immunol.* 157:541-548.

Fanger et al. (1997) Characterization of expression, cytokine regulation and effector function of the high affinity receptor FcγRI (CD64) expressed on human blood dendritic cells. *J. Immunol.* 158: 3090-3098.

Gosselin et al. (1992) Enhanced antigen presentation using Fc gamma receptor (monocyte-macrophage)-specific immunogens. *J. Immunol.* 149(11): 3477-3481.

Sallusto et al. (1994) Efficient presentation of soluble antigen by cultured human dendritic cells is maintained by granulocyte/macrophage colony-stimulating factor plus interleukin 4 and down-regulated by tumor necrosis factor alpha. *J. Exp. Med.* 179: 1109-1118.

Sornasse et al. (1992) Antigen-pulsed dendritic cells can efficiently induce an antibody response in vivo. *J. Exp. Med.* 175: 15-21.

Grouard et al. (1995) Human follicular dendritic cells enhance cytokine dependent growth and differentiation of CD40-activated B cells. *J. Immunol.* 155: 3345-3352.

Clark et al. (1992) Cultured humna follicular dendritic cells: growth characteristics and interactions with B cells. *J. Immunol.* 148(11):3327-3335.

Bosma, M.J., and Carroll, A.M. (1991) The SCID mouse mutant: Definition, characterization and potential uses. *Annu. Rev. Immunol.* 9: 323-350.

Mosier, D.E. (1991) Adoptive transfer of human lymphoid cells to severely immunodeficient mice, models for normal human immune function, autoimmunity, lymphomagenesis and AIDS. *Adv. Immunol.* 50: 303-325.

Walker et al. (1994) The in vivo production of specific human antibodies by vaccination of human-PBL-SCID mice. *Immunology* 83(2): 163-170.

Uchibayasi et al. (1995) A human monoclonal antibody to a human self-antigen, CD2 derived from human peripheral blood lymphocytes engrafted in SCID mice. *Hybridoma* 14(4): 313-321.

Challita-Eid et al. (1998) A B7.1-Antibody Fusion Protein Retains Antibody Specificity and Ability to Activate Via the T Cell Costimulatory Pathway. *J. Immunol.* 160(7): 3419-3426.

Garcia et al. (1997) Limits of the Human-PBL-SCID Mice Model; Severe Restriction of the Vβ T-Cell Repertoire of Engrafted Human T Cells. *Blood* 89(1): 329-336.

* cited by examiner

| Condition | | ΔMFI[b] | | | Mean ΔMFI[c] | ΔΔMFI[d] | p Value[e] |
|---|---|---|---|---|---|---|---|
| | | Donor 1 | Donor 2 | Donor 3 | | | |
| Media | CD1a | 20.7 | 12.1 | 23.3 | 18.7 ± 5.9 | | |
| | CD14 | 9.1 | 9.1 | 22.7 | 13.6 ± 7.9 | | |
| | Class II | 2614 | 3023 | 4034 | 3223.7 ± 731.0 | | |
| | CD40 | 215 | 318 | 453 | 328.7 ± 119.4 | | |
| | B7.1 | 55.2 | 64.9 | 76.3 | 65.5 ± 10.6 | | |
| | B7.2 | 353 | 249 | 260 | 287.3 ± 57.1 | | |
| PSA | CD1a | 19.6 | 9.1 | 18.4 | 15.7 ± 5.7 | -3.0 | 0.28 |
| | CD14 | 4.5 | 4.5 | 44.1 | 17.7 ± 22.9 | 4.1 | 0.39 |
| | Class II | 5560 | 6234 | 7199 | 6331.0 ± 823.8 | 3107.3 | 0.004 |
| | CD40 | 565 | 743.4 | 1348.4 | 885.6 ± 410.6 | 556.9 | 0.043 |
| | B7.1 | 220 | 197.1 | 446.1 | 287.7 ± 137.6 | 222.2 | 0.025 |
| | B7.2 | 586.8 | 639.2 | 615 | 613.7 ± 26.2 | 326.4 | 0.0004 |
| PSA-IgG2a | CD1a | 22.3 | 13.7 | 14.15 | 16.7 ± 4.8 | -2.0 | 0.34 |
| | CD14 | 0 | 0 | 3.9 | 1.3 ± 2.3 | -12.3 | 0.03 |
| | Class II | 3264 | 4186 | 6008.8 | 4486.3 ± 1397 | 1262.6 | 0.12 |
| | CD40 | 277 | 453 | 863 | 531.0 ± 300.0 | 202.3 | 0.17 |
| | B7.1 | 57.8 | 92.5 | 213.4 | 121.2 ± 81.6 | 55.7 | 0.15 |
| | B7.2 | 430 | 358.4 | 419.2 | 402.5 ± 38.8 | 115.2 | 0.02 |

[a] DC from were grown in three sets of triplicate cultures for each of the three random female donors. One set of triplicate cultures from each donor was pulsed with either 25 μg/ml PSA, 25 μg/ml PSA-IgG2a or mock treated on day 6, pooled on day 7, and subjected to flow cytometric analysis as described in *Materials and Methods*. Results shown are for DC gated by forward and side scatter.
[b] ΔMFI is calculated as follows: MFI - MFI of matched isotype controls.
[c] Mean ΔMFI is the average of ΔMFI results generated from three donors ± SD ($n = 3$).
[d] ΔΔMFI is calculated as follows: mean ΔMFI of Ag pulsed cells - mean ΔMFI of control cells.
[e] The paired Student *t* test was used to determine the statistical significance of ΔΔMFI values. A $p<0.05$ was considered to be statistically significant. Data shows significantly greater B7.1, B7.2, CD40, and MHC class II expression on DC pulsed with PSA compared to mock treated control DC. Only B7.2 expression was found to significantly greater on PSA-IgG2a pulsed DC when compared to control DC.

FIGURE 5

Production of Human IgG and IgM in
DC/Ab-PSA Complex Immunized hu-PBL-SCID Mice

Production of Human IgG and IgM in
DC/Ab-PSA Complex Immunized hu-PBL-SCID Mice

METHOD FOR PRODUCING HUMAN ANTIBODIES IN SCID MICE WHICH USES DENDRITIC CELLS PULSED WITH ANTIGEN-ANTIBODY COMPLEXES AND ANTIGEN-ANTIBODY COMPLEXES AS IMMUNIZING AGENTS

This application is a continuation of U.S. patent application Ser. No. 09/149,479 filed Sept. 8, 1998 (abandoned), and claims the benefit of U.S. Provisional patent application No. 60/057,831, filed Sept. 8, 1997.

FIELD OF THE INVENTION

The subject invention provides a novel and reproducible method for producing human monoclonal antibodies to desired antigens, e.g. prostate specific antigen. These monoclonal antibodies, because of their human origin, should be useful therapeutic agents, e.g. for the treatment of human prostate cancer.

BACKGROUND OF THE INVENTION

Antibodies (Ab) that recognize and adhere to proteins on the surface of bacteria, virus or parasites help immune system cells identify, attack and remove them from the body. Similarly, monoclonal Ab (MoAb) that adhere to cancer cells but not to normal cells can be an effective therapy for human cancers. Such MoAbs are generally murine Abs genetically modified to contain human constant regions ("humanized"). However, fully human MoAb are potentially superior to humanized murine MoAb as therapies for human cancer because of their absence of immunogenicity in humans. Human B cells can be stimulated to produce Abs that recognize specific human target proteins. However, previous methods are typically very complex and yield inconsistent results. Therefore, there exists a need in the art for improved methods for producing human monoclonal antibodies.

OBJECTS OF THE INVENTION

It is an object of the invention to obviate the problems of the prior art.

It is a specific object of the invention to provide a novel method for producing human antibodies in severe combined immunodeficiency (SCID) mice.

It is an even more specific object of the invention to provide a novel method for producing human antibodies in SCID mice wherein the immunizing protocol includes the administration of dendritic cells which have been pulsed in vitro with antigen-antibody complexes and/or antigen-antibody complexes.

It is a more specific object of the invention to provide a novel method for producing human antibodies specific to human prostate specific antigen (PSA).

It is an even more specific object of the invention to provide a novel method for producing human antibodies to human PSA in SCID mice wherein the immunization protocol includes the administration of dendritic cells which have been pulsed in vitro with PSA-anti-PSA antibody complexes and/or PSA-anti-PSA antibody complexes.

It is still another object of the invention to provide a novel immunization protocol for producing human antibodies in SCID mice that includes in vivo transformation with Epstein-Barr virus (EBV) during immunization.

BRIEF DESCRIPTION OF THE INVENTION

As discussed in greater detail infra, by judicious experimentation, the present inventors have developed an improved method for producing human antibodies in SCID mice. Specifically, it has been found that immunization of SCID mice with autologous dendritic cells, e.g., autologous peripheral blood dendritic cells that have been pulsed in vitro with a desired antigen, more preferably an antigen-antibody complex, yields high antibody titers wherein such antibodies possess the desired specificity.

Also, it has been found that immunization with antigen-antibody complexes yields improved results, i.e., high serum antibody titers wherein such antibodies exhibit the desired specificity.

Still further, the present invention provides in particular a novel immunization protocol for producing human monoclonal antibodies to prostate specific antigen (PSA). These antibodies, because of their specificity and human origin, should be useful for the treatment of prostate cancer. Because of their human origin, they should possess human antibody effector functions and should elicit no immunogenicity.

DESCRIPTION OF THE FIGURES

FIG. 3 is a FACS analysis of peripheral blood dendritic cells cultured in serum free media. DC were grown in triplicate cultures, harvested on day 7, pooled and subjected to FACS analysis as described in "Materials and Methods". The DC generated from PBMC used to reconstitute the SCIDhu PBL mice were 65% large, MHC class II$^+$/CD33$^+$/CD40$^+$/CD1a$^{lo}$/CD14$^-$ cells with dendritic morphology. The remaining cells were mostly T cells and some B cells. These results are similar to those obtained from cultures generated from 8 individual PBMC donors. All donors generated cultures that were between 50 and 75% CD11c$^{hi}$/CD32$^+$/CD33$^+$/CD40$^+$/CD45RO$^{+/-}$ClassII$^+$/B7.1$^+$/B7.2$^+$DC. DC generated from different donors were heterogeneous for CD1a, CD4, CD14, and CD64 expression (Data not shown).

FIG. 4 is a comparison of MHC and T cell co-stimulatory surface Ag expression by DC cultures. DC were grown in triplicate cultures, harvested on day 7, pooled and subjected to FACS analysis as described in "Materials and Methods". Results show MHC class II, B7.1, B7.2 and CD40 expression was significantly enhanced on DC pulsed with soluble PSA but not PSA-mIG$_{2a}$. Similar results were obtained with DC cultures generated from another donor and pulsed with Tetanus toxoid.

DETAILED DESCRIPTION OF THE INVENTION

The present inventors have developed a novel and reproducible method to stimulate human B cells to make Ab that adhere to desired antigens, e.g. prostate specific antigen (PSA), a protein on the surface of prostate cancer cells. Using these methods, specific human monoclonal antibodies to desired antigens can be cloned, which have applicability in human treatments, e.g., the treatment of prostate cancer.

The advantages of the subject invention are significant.

In particular, these methods are advantageous for the rapid production of fully human monoclonal antibodies for immunotherapy of human diseases.

The major distinguishing differences of the subject protocols compared to prior practices are the use of Ab-antigen (Ag) complexes and autologous dendritic cells (DC) as immunizing adjuvants.

Still another non-obvious distinguishing difference of the subject methods in relation to previous methods is the inclusion of intentional EBV transformation in vivo during the unique DC/Ab-Ag complex immunization steps. Also, the present inventors have determined optimal conditions for Ag boosting SCIDhu PBL mice (using PSA as a model antigen), and high affinity antibodies to PSA using two different donors.

Figure 1:
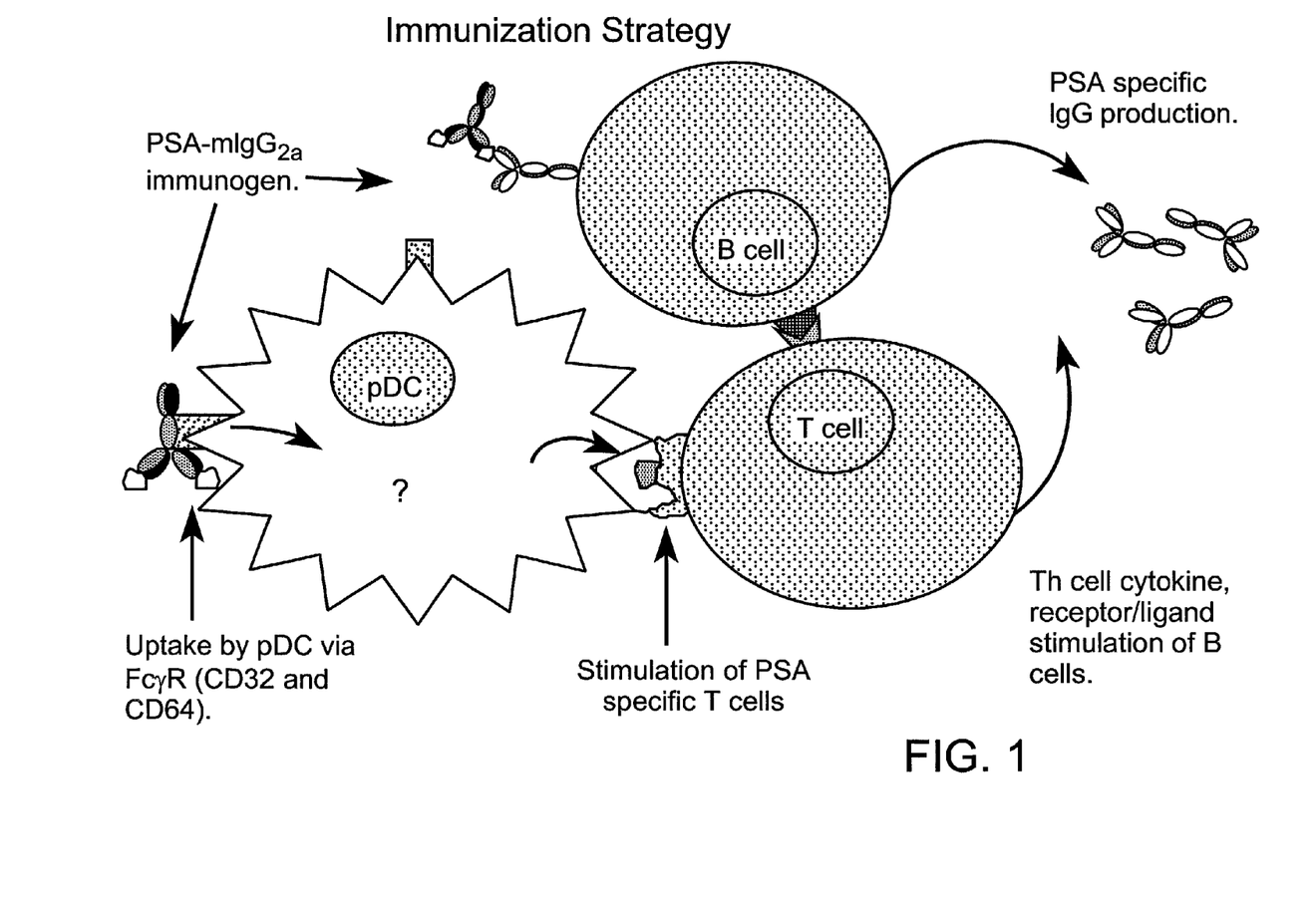
FIG. 1 schematically depicts the immunization strategy of the invention.

In order to generate human anti-PSA specific IgG responses that could be immortalized we have developed a novel SCIDhu mouse immunization protocol (see FIG. 1). See, also, FIG. 2, which is a flow chart summarizing the engraftment and immunization of SCIDhu mice. Briefly, we hoped that complexing antigen to the Fc receptors of dendritic cells (DC) would increase the immunogenicity of the antigen. (However, given the inherent unpredictability with monoclonal antibody manufacture, this result was not assured.) Therefore, we pulsed dendritic cells isolated and expanded from a particular donor with PSA complexed to a mouse anti-PSA IgG$_{2a}$ monoclonal Ab (Ab-PSA complex).

On day 0, SCID's were reconstituted with $10^8$ female PBL's and immunized with 25 mg Ab-PSA complex. Simultaneously, autologous, DC cultures were initiated. The DC were pulsed with 25 mg/ml Ab-PSA complex on day 6, and injected i.p. on day 7. The mice were boosted with 25 mg of Ab-PSA complex on days 7 and 14 and with 25 mg of soluble PSA on day 21. Mice immunized by this method generated PSA specific IgG sera concentrations that were comparable to those induced to Tetanus Toxoid using standard immunization methods (TT in alum). Moreover, these results were reproduced in two separate experiments using different PBMC donors. Therefore, the present immunization protocol is reproducible and therefore should be applicable to different antigens, in particular those involved in human diseases.

As noted, the subject method uses dendritic cells which have been pulsed in vitro with antigen or antigen-antibody complexes as immunizing agents. Dendritic cells (DC) are professional antigen presenting cells (APC) that initiate an immune response. Recently, several methods have been developed to generate human DC from peripheral blood mononuclear cell (PBMC) derived progenitor cells in vitro. These different culture methods yield several DC subtypes with heterogeneous morphology, phenotype, and function. However, all these DC subtypes have been shown to be potent stimulators of naive Ag-specific T cells. This is due in large part to the fact that DC express class I and II MHC and co-stimulatory cell surface molecules B7.1 and B7.2. In addition, human DC pulsed with weakly immunogenic tumor associated antigens (TAA) are capable of stimulating TAA specific cytotoxic T lymphocyte (CTL) proliferation and cytotoxicity, in vitro, thus illustrating both their potency as APC and their potential utility as tumor specific vaccines.

DC derived from PBMC and cultured with GM-CSF and IL-4 express both the high affinity IgG receptor FcγRI (CD64) and the low affinity IgG receptor FcγRII (CD32) at varying levels (3,11). Both CD64 and CD32 have been shown to mediate uptake of Ag by DC. Targeting Ag to FcγR on human monocytes and DC via monoclonal antibody (mAb)-Ag complexes reduces the amount of Ag required for Ag specific T cell activation as much as 1000-fold.

Although many recent studies have analyzed human T cell activation by DC, what is not clear is whether in vitro generated DC are capable of stimulating a primary humoral immune response. DC isolated from mouse spleen and pulsed with myoglobin were capable of stimulating a primary humoral immune response in syngeneic mice, but mouse splenic DC may have different immunostimulatory effector functions than DC derived from human peripheral blood. Follicular DC (FDC)-lymphocyte clusters isolated from human tonsil enhanced growth and Ig production by CD40 activated human B cells, in vitro. However, tonsillar FDC are phenotypically and morphologically distinct from peripheral blood derived DC and, therefore, are likely to have different effector functions as well.

SCID mice are deficient in mature lymphocytes, Ig production and lymphocyte mediated immune responses due to defective Ig and T cell receptor gene rearrangement. SCID mice reconstituted with human peripheral blood lymphocytes (SCIDhu PBL mice) can be effective models of recall antigen directed Ig production by human B cells. However, it is very difficult to stimulate neo-Ag, self-Ag or TAA specific primary immune responses and IgG production in SCIDhu PBL mice.

In this study we characterized the phenotype of DC generated from PBMC in low protein, serum free media. We then assessed the ability of serum free cultured DC to stimulate a prostate specific antigen (PSA) specific, primary humoral immune response by SCIDhu PBL mice. We showed that DC pulsed with PSA completed to a mouse IgG$_{2a}$ specific for human PSA (PSA-mIg G$_{2a}$) can induce PSA specific human IgG production in SCIDhu PBL mice. SCIDhu PBL mice immunized with soluble PSA pulsed DC did not produce PSA specific IgG. These results suggest that the mechanism by which DC acquired Ag altered DC expression and immunostimulating effector functions. Different Ag acquisition mechanisms yield different co-stimulating molecule surface expression and subsequent immunostimulatory effector functions by DC.

EXAMPLE

The following materials and methods were used.

DC Generation in Serum Free Cultures

PBMC were obtained from healthy donors by leukophoresis or by venapuncture into heparinized tubes. RBC were removed from residual PBMC by hypotonic lysis in Gey's lysis buffer prior to freezing in 50% human serum, 40% Iscoves complete media (Iscove's modified Delbucco's media (Irvine Scientific, Santa Ana, Calif.) plus sodium pyruvate, minimal essential amino acids, L-glutamine (Sigma, St. Louis, Mo.) and gentamicin (Gibco BRL, Grand Island, N.Y.)) and 10% DMSO (Sigma). Frozen PBMC were stored in $LN_2$. DC were grown essentially as described by Romani et al, except that Iscove's complete was supplemented with 2% Nutridoma® HU (Boehringer Mannheim Corporation, Indianapolis, Ind.) instead of 10% fetal bovine serum. Freshly isolated and thawed PBMC were purified by Histopaquel (Sigma) gradient separation, washed and plated at $5 \times 10^6$ cells/ml in IN2 at 37° C. for 2 hrs. Non-adherent cells were gently removed with the media, additional 37° C. IN2 was added and the cells were incubated at 37° C. for 5 additional minutes. Non-adherent cells were again gently removed and the residual cells were cultured in IN2 supplemented with 500 U/ml IL-4 and 800 U/ml GM-CSF (Genzyme, Inc., Cambridge, Mass.). Cultures were fed with additional cytokines on day 3. Human PSA specific mouse monoclonal $IgG_{2a}$ (Clone 10-P20; Fitzgerald Industries International Inc., Concord, Mass.) was complexed with >99% pure PSA (Fitzgerald Industries International) at equimolar ratios at 4° C. overnight (PSA-$mIgG_{2a}$). The DC enriched cultures were pulsed with 25 µg/ml (final concentration) PSA, PSA-$migG_{2a}$ or an equivalent volume of IN2 on day 6 and non-adherent cells were harvested on day 7.

Flow Cytomnetric Analysis

Figure 3:
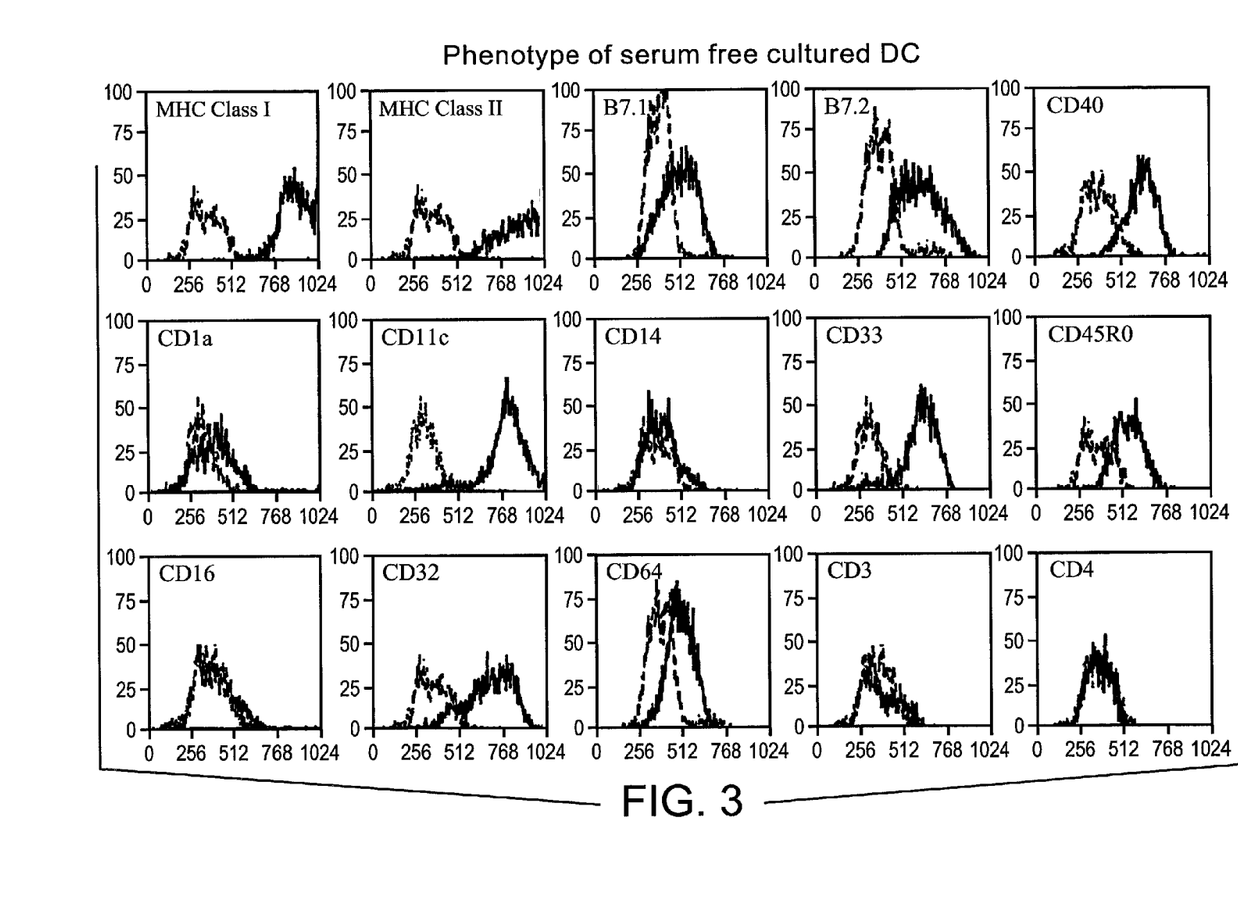

The following FITC and PE labeled monoclonal antibodies (mAb) were used: anti-HLA DR, DP, DQ, anti-CD 1a, anti-CD3, anti-CD11c, anti-CD16, anti-CD32w (FcγRII), anti-CD33, anti-CD40, anti-CD45RO, anti-CD64 (FcγRI), anti-CD86 (B7.2), (Pharmingen, San Diego, Calif.), anti-CD4, anti-CD 14, anti-CD80 (B7.1), PE-labeled isotype controls (Becton and Dickinson, San Jose, Calif.), anti-ABC, and FITC labeled isotype controls (Harlan Bioproducts for Science, Inc., Indianapolis, Ind.). Day 7 DC enriched cultures and single cell isolates from SCIDhu PBL mouse tissues were washed and resuspended in 4° C. FACS buffer (1% BSA, 1×PBS, 0.1% Na Azide and 40 µg/ml human IgG) at $1 \times 10^6$ cells/ml. The cells were then aliquoted and stained for 45 minutes with mAb diluted to the manufacturers' recommended concentration. The cells were washed twice in FACS buffer and data was acquired on a FACScan® (Becton Dickinson). Data was analyzed using Lysis 1® (Becton Dickinson) or, F cap List® (Soft FlowHungary, Inc., Pécs, Hungary) software. Specific reactivity data shown as ΔMFI is calculated as follows: MFI of FITC or PE labeled specific mAb-MFI of isotype and fluorochrome matched mAb control. These results are contained in FIGS. 3 and 4.

SCID Mouse Engraftment and Immunization

PBMC were obtained from healthy female donors by leukophoresis. RBC were removed by hypotonic lysis in Gey's lysis solution. Residual PBMC were frozen and stored as described above. Four to six week old male Fox Chase ICR SCID™ mice (Taconic, Germantown, N.Y.) were housed, fed and handled according to established protocols for immunodeficient strains. Mice were engrafted with $10^8$ PBMC, i.p., on day 0. Autologous DC cultures were initiated on day 0 as described above. Group F mice were immunized with 25 µg of PSA-$mIgG_{2a}$ complex weekly, $7 \times 10^6$ thawed autologous PBMC on day 7 and then boosted with 25 µg PSA on day 21. Group G Mice were immunized with 25 µg of soluble PSA weekly and $7 \times 10^6$ PSA pulsed DC enriched cells on day 7. Group H mice were immunized with 25 µg of PSA-$IgG_{2a}$ complex weekly, $7.5 \times 10^6$ PSA-$mIgG_{2a}$ pulsed DC enriched cells on day 7 and then boosted with 25 µg PSA on day 21. Sera was collected on days 14 and 28. Mice were sacrificed and spleens and lymph nodes were collected on day 28. Some spleens were laterally bisected and single cells isolated from one half were analyzed by flow cytometry as described above. The remaining spleens and LN were embedded in OCT compound (Sukura Finetek, Inc., Torrance, Calif.) and then simultaneously frozen and fixed in $LN_2$ chilled 2-methylbutane (Sigma) for immunohistochemical staining.

ELISAs

Figure 5:
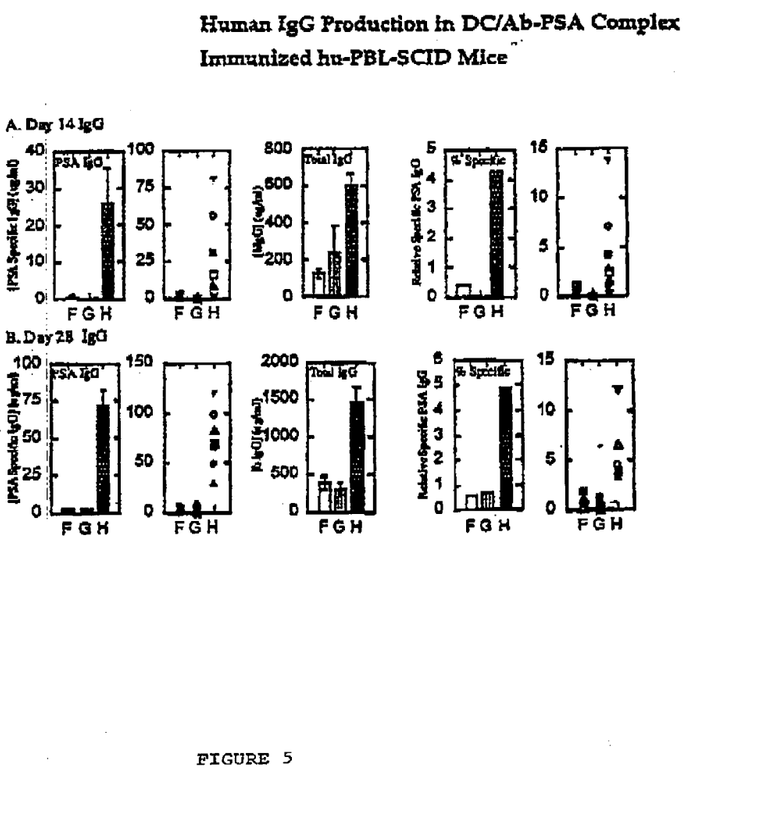
FIG. 5 shows the amounts of total and PSA specific human IgM and IgG in sera of SCIDhu PBL mice. Sera was collected on days 14 and 28. Total and PSA specific human IgG were quantitated by ELISA. The values shown in FIGS. 5A, 5C, 5D, and 5E are the average of 8 mice per group. Error bars represent±Std. Dev.
Figure 5A:
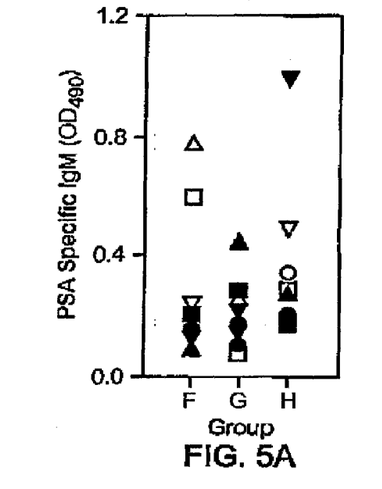
FIGS. 5A and 5B: Relative amounts of PSA specific IgM (FIG. 5A) and concentrations of human IgM (µg/ml) (FIG. 5B) in sera of individual mice of groups F, G, and H.
Figure 5B:
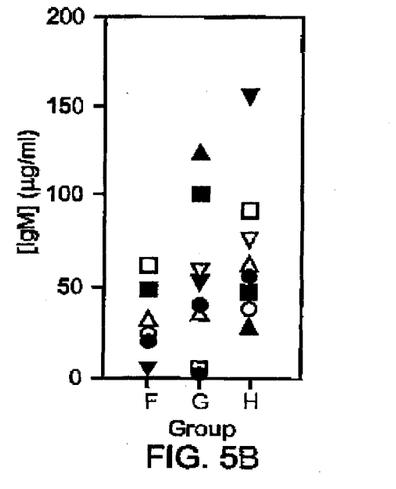

Human Ig sera concentrations were assayed by quantitative ELISAs. ELISAs were performed in 96 well Immulon 2 "U" ELISA plates (Dynatech Laboratories, Inc., Chantilly, Va.). Human IgG and IgM ELISA plates were coated with 2 µg/ml polyclonal goat anti-human IgG or goat anti-human IgM (Southern Biotechnology Associates, Inc., Birmingham, Ala.) in bicarbonate buffer (pH 9.3) overnight. PSA specific IgG plates were coated with 99% pure PSA at 4 µg/ml in bicarbonate buffer. PSA specific IgG was quantitated using a mouse monoclonal $IgG_1$ specific for PSA (clone ERPR8, ICN, Costa Mesa, Calif.) as a standard. Incubations were done at RT in serially diluted duplicate wells. Binding of Ig was detected by horseradish peroxidase (HRP) conjugated polyclonal goat anti-human IgM-HRP, polyclonal goat anti-human IgG-HRP or polyclonal goat anti-mouse IgG-HRP secondary antibody (Southern Biotechnology Associates) incubation and subsequent enzymatic development of o-phenylenediamine dihydrochloride (Sigma) substrate. Reactions were quenched with 4N $H_2SO_4$ and the plates were read on a ELISA plate reader at $OD_{490}$. The concentration of human Ig in SCIDhu PBL sera was quantitated by comparison of SCIDhu PBL serum $OD_{490}$ values with serially diluted standard curves. These results are contained in FIG. 5.

To confirm the PSA binding specificity of group H sera IgG pooled sera from four group H mice was diluted 1:15 (50 µg/ml total IgG final concentration) and 1:20 (50 µg/ml total IgG final concentration) into triplicate wells containing serially diluted concentrations of soluble PSA. Soluble PSA induced inhibition of PSA specific binding by group H sera and by an equivalent concentration of control human IgG (Zymed, Inc.) was assayed using polyclonal goat anti-human IgG-HRP, as described above. These ELISA results are contained in FIG. 6.

Immunohistochemistry Analysis

Histologic and human lymphocyte specific antibody (CD3 and CD19) staining of frozen and fixed SCIDhu PBL mouse tissues was contracted to BioPharMaceutical Support Services (Pharmingen).

Immunoblot Analysis

These experiments are ongoing.

Example 1

Human IgG Production in DC/Ab-PSA Complex Immunized SCIDhu PBL Mice Mouse Monoclonal IgG.

Figure 5C:
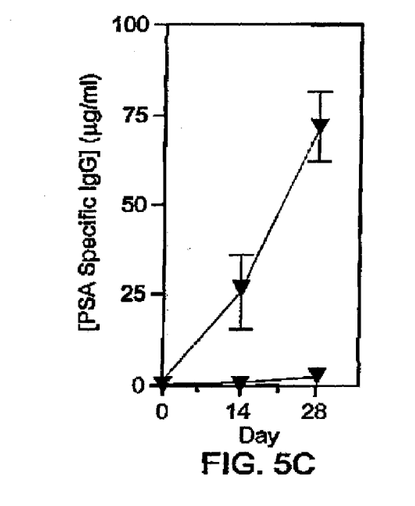
FIGS. 5C and 5F: Average concentration of PSA specific IgG (µg/ml) for day 0 to day 28 (FIG. 5C); and the amounts of PSA specific IgG (µg/ml) produced by individual mice of groups F, G, and H on day 28 (FIG. 5F). PSA specific IgG was quantitated using a mouse monoclonal IgG specific for human PSA as a standard. Only Group H produced PSA specific IgG.
Figure 5D:
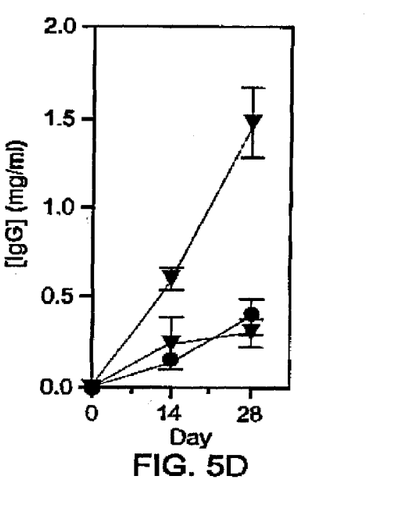
FIGS. 5D and 5G: Average total human IgG (mg/ml) for day 0 to day 28 (FIG. 5D); and the amounts of human IgG (mg/ml) produced by individual mice of groups F, G, and H on day 28 (FIG. 5G). Group H mice IgG sera concentrations ranged between 0.56 and 2.19 mg/ml IgG by day 28. IgG sera concentrations in groups F and G control mice ranged between 8 and 840 µg/ml IgG by day 28.
Figure 5E:
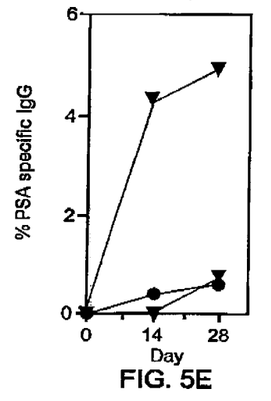
FIGS. 5E and 5H: Average percent PSA specific IgG for day 0 to day 28 (FIG. 5E); and the percentages of PSA specific IgG produced by individual mice of groups F, G, and H on day 28 (FIG. 5H). The percent of PSA specific IgG was calculated as follows: [PSA specific IgG]/[total IgG]× 100.
Figure 5F:
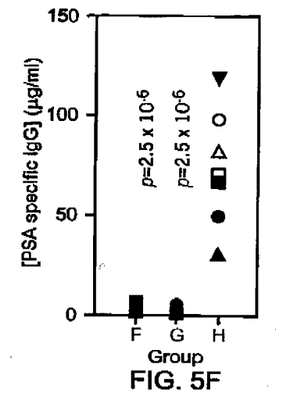
Figure 5G:
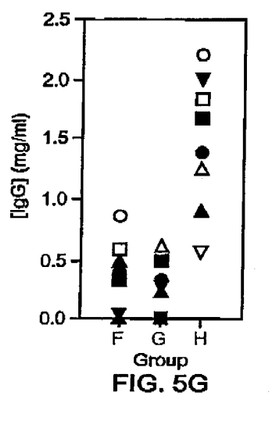
Figure 5H:
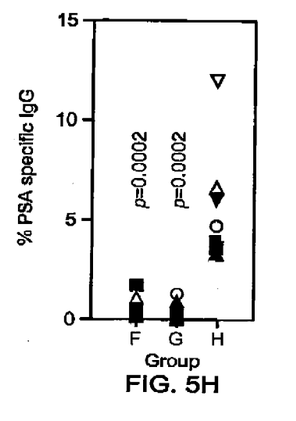

Antibody (Cat. No. 10-P20; Fitzgerald Industries Inc.) was complexed with PSA at equimolar ratios at 4° C. over night (Ab-PSA complex) and then dialyzed to remove azide. Autalogous peripheral blood dendritic cells (pDC) were grown in serum free media and pulsed with either 25 µg/ml soluble PSA or Ab-PSA complex. All mice received $10^8$ PBMC i.p. on day 0. Each group consisted of 8 mice. Group F mice were immunized with 25 g of Ab-PSA complex weekly and with 25 µg PSA on Day 21. Group G mice were immunized with 25 µg of soluble PSA weekly and $7 \times 10^6$ soluble PSA pulsed pDC on day 7. Group H mice were immunized with 25 µg of Ab-PSA complex weekly, $7.5 \times 10^6$ Ab-PSA pulsed pDC on day 7 and then 25 µg PSA on Day 21. Results for the period from day 0 to day 28 are summarized in FIGS. 5C–5E. FIG. 5C shows average concentrations of PSA specific IgG (µg/ml); FIG. 5D shows average total human IgG (mg/ml); and FIG. 5E shows average percent PSA specific IgG, in sera of the mice of groups F, G, and H. Error bars represent±Std. Dev.

Figure 2:
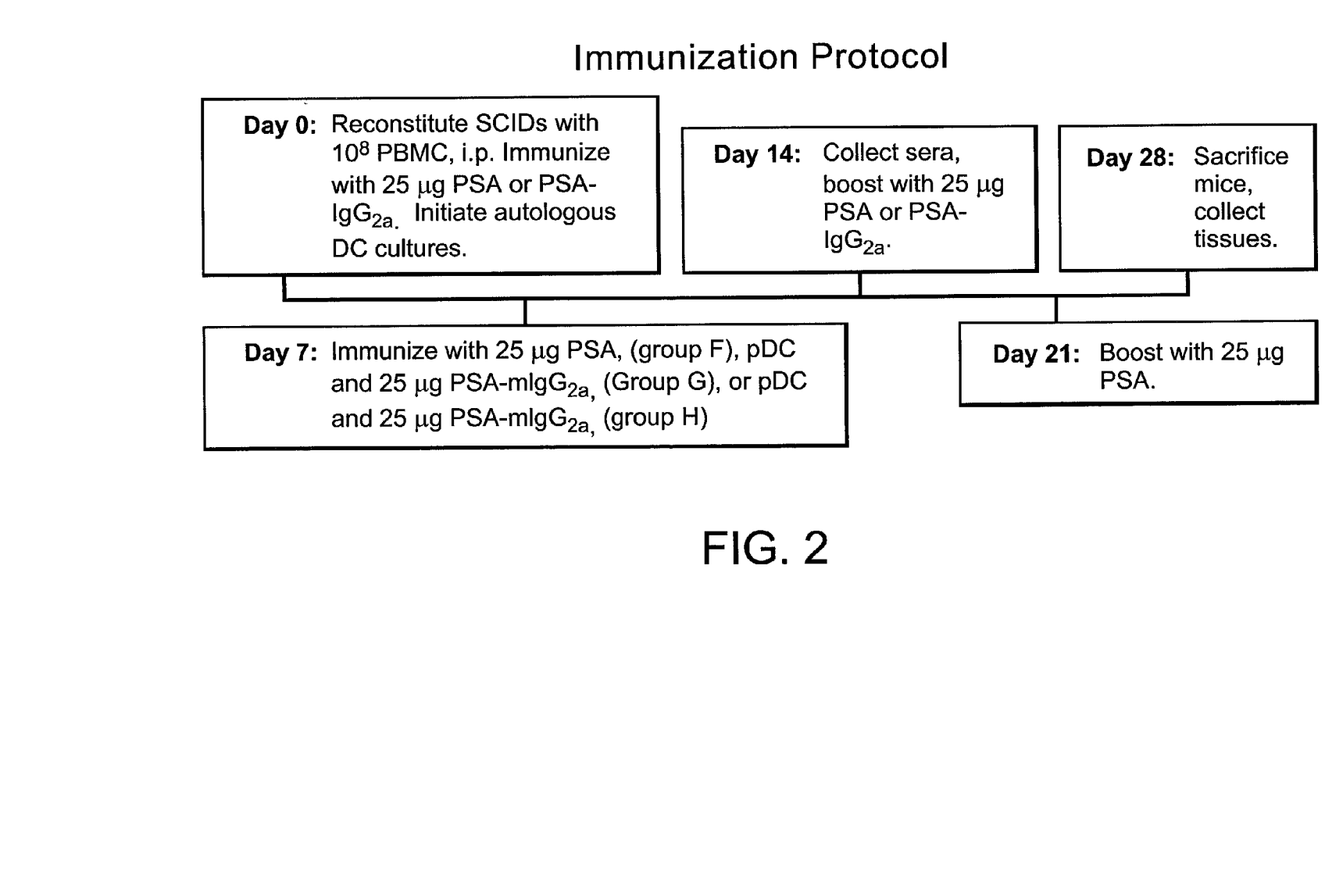
FIG. 2 is a flow chart summarizing the engraftment and immunization of SCIDhu PBL mice.

The immunization method described in FIG. 2 for group H enhanced human lymphocyte engraftment in SCIDhu PBL mice. On the average, six times more human T cells were detected per spleen and more enlarged lymph nodes (LN) were isolated from group H mice than from either control group (see Table, below). Importantly, the enhanced engraftment and Ig production was not induced at the expense of enhanced xenogeneic graft versus host disease (XGVHD), as has been reported in other "enhanced" SCIDhu systems.

TABLE

Summary of Engraftment

| Group | Total Spleen Cells Number* | % human CD3+ Cells^ | % human CD19+ Cells^ | No. of Mice with enlarged LN/group |
|---|---|---|---|---|
| F | $1.69 \pm 0.26 \times 10^8$ | $2.30 \pm 0.67$ | <2% | 2/8 |
| G | $1.58 \pm 0.32 \times 10^8$ | $2.93 \pm 0.34$ | <2% | 4/8 |
| H | $3.04 \pm 0.60 \times 10^8$ | $8.93 \pm 4.32$ | <2% | 7/8 |

Mice immunized as described in FIG. 2 were sacrificed on day 28. Spleens and LN were collected from all mice. Spleens were divided in half. One half was used to determine cell numbers and to do FACS analysis (3 mice each group). The other half of the spleens and all the isolated LN were fixed and frozen for histologic analysis. Spleen cell number and percent human T cells are shown±Std Dev. (p>0.5). *; average of 8 Mice. ô; average of 3 mice.

Histologic antibody staining data (frozen/fixed slides were stained with a-hCD3 and a-hCD19) showed that Group H mice had many more human T and B cells in enlarged peripheral LN compared to control mice. Also, spleens from group H mice had more localized B cell engraftment than control mice (data not shown).

The specificity of the PSA IgG response by group H mice was confirmed by comparison with non-responding Group F sera, control human IgG and by competition of sera binding by soluble PSA.

Example 2

Specificity of Antibody Responses Obtained in Ab-PSA/pDC Immunized SCIDhu PBC Mice.

In this Example, the relative PSA specificity of pooled sera from group H mice, control hIgG and group F serum was measured and is shown in FIG. 6.

Figure 6A:
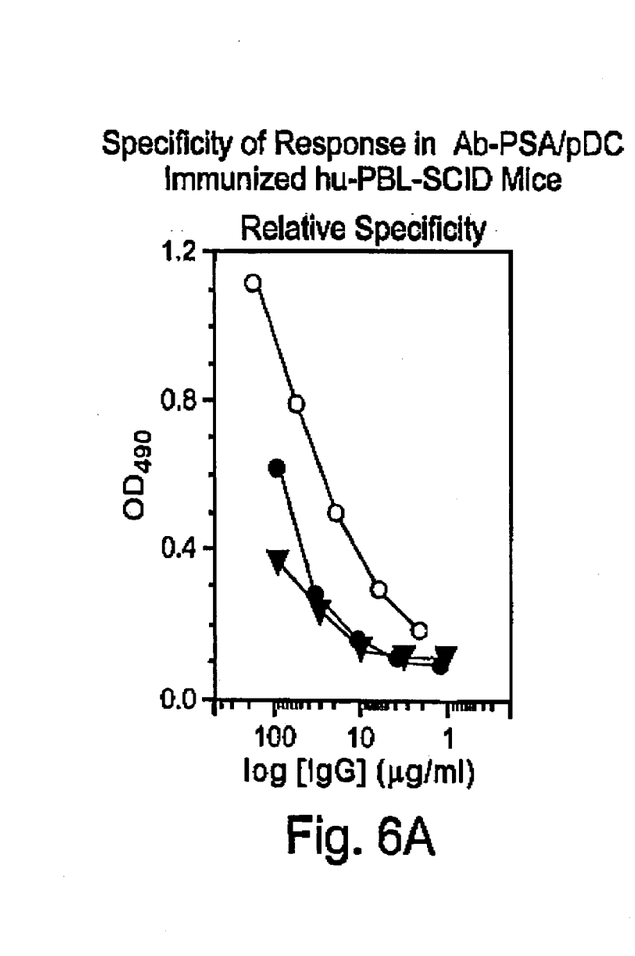
FIG. 6 is an analysis of PSA specificity of group H sera IgG. A. Relative PSA specificity. Human IgG in group H sera binds PSA ten times greater than the non-specific binding generated by group F sera with an equivalent concentration of IgG or by an equivalent concentration of purified human IgG. B. Soluble PSA competition ELISA. Soluble PSA inhibits the binding of group H sera IgG in a concentration dependent manner.
Figure 6B:
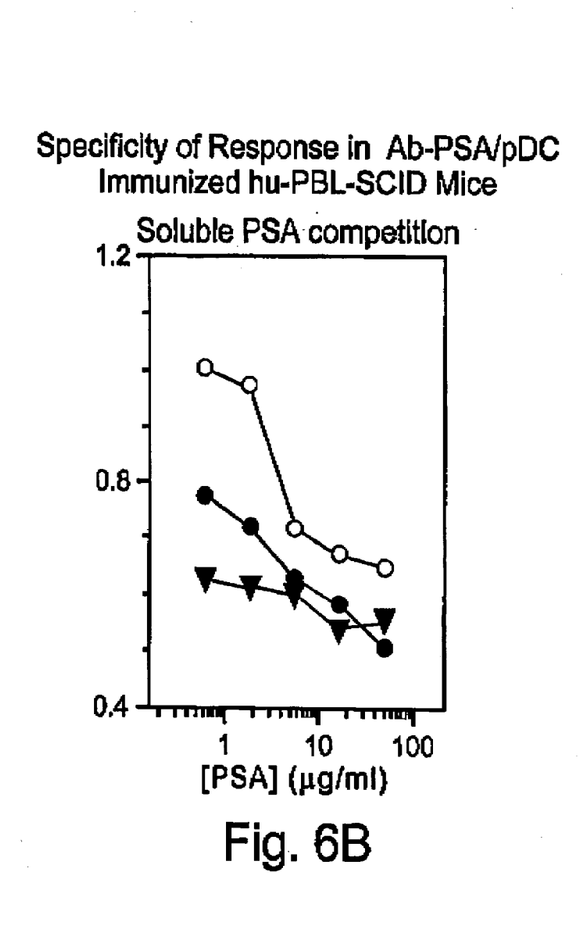

FIG. 6A shows relative PSA specificity of pooled sera from group H mice, control hIgG and group F serum. In this Figure, open circles represent pooled group H serum, and closed circles purified hIgG. The triangles represent mouse F1.1 serum. The data shows that group H serum binds PSA 10 times greater than equal concentrations of either control hIgG. Panel FIG. 6B shows the inhibition of group H sera specific binding by soluble PSA. The open circles represent pooled group H serum diluted 1:15 (120 µg/ml). The closed circles represent pooled group H serum diluted 1;20 (90 µg/ml). The triangles represent purified hIgG control, (90 µg/ml). The data shows that pooled group H sera binding can be inhibited by soluble PSA to $OD_{490}$ values obtained by an equal concentration of control hIgG in a dose dependent manner.

CONCLUSIONS

Therefore, these results demonstrate that DC pulsed with antigen-antibody complexes induced PSA specific Ab responses in SCIDhu PBL mice better than previous immunization protocols. Moreover, the results demonstrate that when such pulsed DC are administered in combination with Ab-antigen complexes, that significant enhancement of total specific (>35 fold) and relative specific (>10-fold) PSA IgG responses in SCIDhu PBL mice is obtained (compared to either immunization strategy performed separately). Also, this novel immunization strategy enhanced human lymphocyte engraftment without enhancing XGVHD as in other "enhanced" SCIDhu systems. Moreover, this method was reproducible in three separate experiments using different PBMC donors.

This approach and the technology developed around it is significant as it enables rapid, reproducible production of clinically superior products (human monoclonal antibodies) compared to antibodies based on rodent antibodies). These human monoclonal antibodies are useful for immunotherapy or immunoprophylaxis, e.g., treatment or prevention of of cancer and viral infections.

The described methodology should be useful for generating human MoAb specific to any relevant target antigen (e.g., Macrophage Inhibitory Factor, E7 antigen, CEA, HIV, etc.). However, being a biological system, it is impossible to predict with absolute certainty the extent of variation of the conditions or parameters that will provide optimal results for different antigens, e.g., the exact number of cells or the exact quantity of Ab-PSA complex that results in optimal antibody production or specificity. However, this can be determined by one of ordinary skill using routine optimization.

The preferred antigens will comprise those expressed by human diseases treatable by monoclonal antibodies (wherein treatment includes therapeutic and prophylactic therapy), e.g., cancers, parasitic infections and viral infections. Examples of diseases treatable by human monoclonal antibodies include, by way of example, cancers such as breast, brain, cervical, ovarian, prostate, bladder, pancreatic, myeloma, kidney, colorectal, nasoparingeal, endometrial, lung, liver, leukemia, lymphoma, colon, stomach, skin, among others, viral diseases, including those caused by HIV, hepatitis, papillomavirus, respiratory syncytial virus, herpes, etc., and parasitic diseases, e.g., malaria.

In the preferred embodiments, the antigen will be selected from melanocytic differentiation antigens, e.g., gp100 (Kawakami et al, *J. Immunol.*, 154:3961–3968 (1995); Cox et al, *Science*, 264:716–719 (1994)), MART-1/Melan A (Kawakami et al, *J. Exp. Med.*, 180:347–352 (1994); Castelli et al, *J. Exp. Med.*, 181:363–368 (1995)), gp75 (TRP-1) (Wang et al, *J. Exp. Med.*, 186:1131–1140 (1996)), and Tyrosinase (Wolfel et al, *Eur. J. Immunol.*, 24:759–764 (1994); Topalian et al, *J. Exp. Med.*, 183:1965–1971 (1996)); melanoma proteoglycan (Hellstrom et al, *J. Immunol.*, 130:1467–1472 (1983); Ross et al, *Arch. Biochem Biophys.*, 225:370–383 (1983)); tumor-specific, widely shared antigens, e.g., antigens of MAGE family, for example, MAGE-1, 2, 3, 4, 6 and 12 (Van der Bruggen et al, *Science*, 254:1643–1647 (1991); Rogner et al, *Genomics*, 29:729–731 (1995)), antigens of BAGE family (Boel et al, *Immunity*, 2:167–175 (1995)), antigens of GAGE family, for example, GAGE-1, 2 (Van den Eynde et al, *J. Exp. Med.*, 182:689–698 (1995)), antigens of RAGE family, for example, RAGE-1 (Gaugler et al, *Immuno-genetics*, 44:323–330 (1996)), N-acetylglucosaminyltransferase-V (Guilloux et al, *J. Exp. Med.*, 183:1173–1183 (1996)), and p15 (Robbins et al, *J. Immunol.*, 154:5944–5950 (1995)); tumor specific mutated antigens; mutated β-catenin (Robbins et al, *J. Exp. Med.*, 183:1185–1192 (1996)), mutated MUM-1 (Coulie et al, *Proc. Natl. Acad. Sci. USA*, 92:7976–7980 (1995)), and mutated cyclin dependent kinases-4 (CDK4) (Wolfel et al, *Science*, 269:1281–1284 (1995)); mutated oncogene products: p21 ras (Fossum et al, *Int. J. Cancer*, 56:40–45 (1994)), BCR-abl (Bocchia et al, *Blood*, 85:2680–2684 (1995)), p53 (Theobald et al, *Proc. Natl. Acad. Sci. USA*, 92:11993–11997 (1995)), and p185 (HER2/neu (Fisk et al, *J. Exp. Med.*, 181:2109–2117 (1995)); Peoples et al, *Proc. Natl. Acad. Sci. USA*, 92:432–436 (1995)); mutated epidermal growth factor receptor (EGFR) (Fugimoto et al, *Eur. J. Gynecol. Oncol.*, 16:40–47 (19965));, Harris et al, *Breast Cancer Res. Treat*, 29:1–2 (1994)); carcinoembryonic antigens (CEA) (Kwong et al, *J. Natl. Cancer Inst.*, 85:982–990 (1995)); carcinoma associated mutated mucins, for example, MUC-1 gene products (Jerome et al, *J. Immunol.*, 151:1654–1662 (1993), Ioannides et al, *J. Immunol.*, 151:3693–3703 (1993), Takahashi et al, *J. Immunol.*, 153:2102–2109 (1994)); EBNA gene products of EBV, for example, EBNA-1 gene product (Rickinson et al, *Cancer Surveys*, 13:53–80 (1992)); E7, E6 proteins of human papillomavirus (Ressing et al, *J. Immunol.*, 154:5934–5943, (1995)); prostate specific antigens (PSA) (Xue et al, *The Prostate*, 30:70–78 (1997)); prostate specific membrane antigen (PSMA) (Israeli et al, *Cancer Res.*, 54:1807–1811 (1994)); PCTA-1 (Sue et al, *Proc. Natl. Acad. Sci. USA*, 93:7252–7257 (1996)); idiotypic epitopes or antigens, for example, immunoglobulin idiotypes or T cell receptor idiotypes (Chen et al, *J. Immunol.*, 153:4775–4787 (1994); Syrengelas et al, *Nat. Med.*, 2:1038–1040 (1996)).

The antigen will preferably be administered to a SCID mouse in the form of an antigen-antibody complex as described supra. Also, as described above, the antigen or more preferably antigen-antibody complex will be used for in vitro priming of autologous dendritic cells, e.g., autologous peripheral blood dendritic cells. The amount and duration of such in vitro priming will be that which results in an enhancement of human antibody production, when the resultant primed dendritic cells are used as immunizing agents in SCID mice. As disclosed, preferably SCID mice will be immunized with autologous dendritic cells which have been pulsed in vitro with an antigen-antibody complex and further immunized with such antigen-antibody complex as this has been shown to confer synergistic benefits (enhance total antisera-specific antibody response and relative specific IgG antibody response).

Also, it is desirable that EBV transformation be effected during immunization. After immunization, human antibody secreting cells will be isolated from such SCID mice and used to clone human monoclonal antibodies. This may be effected by known methods.

Monoclonal antibodies possessing desirable properties (minimum antigen binding affinity and avidity) obtained by such methods are useful as human therapeutics and prophylactics. These human monoclonal antibodies will be administered by known methods, e.g., systemically or parenterally, e.g., orally, subcutaneously, intravenously, intramusculatory, topically, by infusion, to patients in need of such treatment.

The administered dosage will be a dosage that results in therapeutic or prophylactic benefits. Generally, such dosage will range from about 0.001 to 100 mg/kg, more preferably 0.01 to 50 mg/kg, still more preferably 0.1 to 5 mg/kg body weight. Moreover, such dosage will vary dependent upon the condition of the patient, the disease condition, whether other therapies are also being effected, among other factors.

Typically, the antibody will be administered in combination with a pharmaceutically acceptable carrier or excipient, e.g., phosphate buffered saline, optionally in combination with adjuvants that enhance humoral or CTL immunity.

In the case of prostate specific antigen specific antibodies, these antibodies will be used for the treatment or prevention of prostate cancer as this is a known antigen expressed during prostate cancer.

What is claimed is:

1. A method for producing human IgG antibodies in a severe combined immunodeficiency (SCID) mouse which has been transplanted with human immune cells, which comprises injecting human peripheral blood lymphocytes (PBL) into a SCID mouse to produce a SCIDhu PBL mouse that contains human B cells that produces antibodies specific for an antigen with which the SCIDhu PBL mouse is immunized;

immunizing the SCIDhu PBL mouse with antibody-antigen complex; and immunizing the SCIDhu PBL mouse with human dendritic cells which have been contacted (pulsed) in vitro with the antigen-antibody complex.

2. The method of claim 1, wherein the dendritic cells comprise autologous peripheral blood dendritic cells.

3. The method of claim 1, which includes Epstein-Barr virus (EBV) transformation during the immunization step.

4. The method of claim 1, wherein said SCIDhu PBL mouse is immunized with antigen-antibody complex prior to immunization with dendritic cells which have been contacted (pulsed) with antigen-antibody complex.

5. The method of claim 1, wherein a first immunization with antigen-antibody complex is followed by a second immunization with human dendritic cells which have been contacted (pulsed) with antigen-antibody complex that is effected about 1 to 15 days after the fist immunization.

6. The method of claim 5, wherein said second immunization is effected about 7 days after the first immunization.

7. The method of claim 4, which further includes at least one additional immunization ("boosting") wherein the SCIDhu PBL mouse is administered antigen or antigen-antibody complex.

8. The method of claim 7, wherein a boosting step is effected about a week after the first immunization.

9. The method of claim 8, wherein another boosting step is effected about two weeks after the first immunization.

10. The method of claim 9, wherein another boosting step is effected about three weeks after the first immunization.

11. The method of claim 1 which results in human IgG antibody titers in the serum of the SCIDhu PBL mouse ranging from about 0.56 to about 2.19 mg/ml.

12. The method of claim 1, wherein the dendritic cells are generated from peripheral blood mononuclear cell-derived progenitor cells.

13. The method of claim 12, wherein the dendritic cells are generated by inducing the differentiation of peripheral blood mononuclear cell-derived progenitor cells into dendritic cells in vitro.

14. The method of claim 1, wherein the antibody of the antigen-antibody complex is a murine IgG antibody that comprises an Fc portion that binds to an Fc receptor of a human dendritic cell.

15. The method of claim 14, wherein the antibody of the antigen-antibody complex is a murine $IgG_{2a}$ antibody.

16. The method of claim 1, wherein the antigen of the antigen-antibody complex is a human tumor-associated antigen.

17. The method of claim 16, wherein the antigen is p185 (HER/neu) and the antibody is an anti-p185 antibody.

* * * * *